(12) United States Patent
Roschak et al.

(10) Patent No.: US 11,090,039 B2
(45) Date of Patent: Aug. 17, 2021

(54) NONINVASIVELY ADJUSTABLE SUTURE ANCHORS

(71) Applicant: NuVasive Specialized Orthopedics, inc., San Diego, CA (US)

(72) Inventors: Edmund J. Roschak, Mission Viejo, CA (US); Thomas B. Buford, Laguna Beach, CA (US); Blair Walker, Mission Viejo, CA (US)

(73) Assignee: NuVasive Specialized Orthopedics, Inc., San Diego, CA (US)

(*) Notice: Subject to any disclaimer, the term of this patent is extended or adjusted under 35 U.S.C. 154(b) by 77 days.

(21) Appl. No.: 16/257,526

(22) Filed: Jan. 25, 2019

(65) Prior Publication Data
US 2019/0150913 A1 May 23, 2019

Related U.S. Application Data

(63) Continuation of application No. 14/447,391, filed on Jul. 30, 2014, now Pat. No. 10,226,262.
(Continued)

(51) Int. Cl.
*A61B 17/04* (2006.01)
*A61B 17/00* (2006.01)

(52) U.S. Cl.
CPC ............ *A61B 17/0401* (2013.01); *A61B 2017/00876* (2013.01); *A61B 2017/044* (2013.01);
(Continued)

(58) Field of Classification Search
CPC .. A61B 17/86–17/8695; A61B 17/04–17/0493
(Continued)

(56) References Cited

U.S. PATENT DOCUMENTS

| 5,429,638 A | 7/1995 | Muschler et al. |
| 5,626,579 A | 5/1997 | Muschler et al. |

(Continued)

FOREIGN PATENT DOCUMENTS

| HU | 223454 B1 | 4/2002 |
| HU | 3895 U | 2/2011 |
| WO | WO 2013-066946 | 5/2013 |

OTHER PUBLICATIONS

U.S. Appl. No. 61/113,086, filed Nov. 10, 2008, Pool, et al.
(Continued)

*Primary Examiner* — Matthew J Lawson
(74) *Attorney, Agent, or Firm* — Hoffman Warnick LLC

(57) ABSTRACT

In one embodiment, an adjustable implant system includes a bone anchor having first and second ends, a bone engagement surface adjacent the first end, and a housing extending between the first and second ends. The adjustable implant system can further include a non-invasively actuatable driving element within the housing and coupled to an adjustment component configured to couple to a flexible elongate tension member which is capable of engaging a patient's soft tissue (e.g., rotator cuff or ACL). Non-invasive actuation of the driving element can cause the adjustment component to change the amount of tension on the flexible elongate tension member and consequently on the patient's soft tissue. The adjustable implant system can include an external adjustment device configured to be placed on or adjacent the patient's skin and comprising at least one energy transferring component configured to energize/actuate the driving element inside the housing of the adjustable implant.

19 Claims, 10 Drawing Sheets

Related U.S. Application Data

(60) Provisional application No. 61/860,668, filed on Jul. 31, 2013.

(52) U.S. Cl.
CPC ............... A61B 2017/0409 (2013.01); A61B 2017/0414 (2013.01); A61B 2017/0453 (2013.01); A61B 2017/0458 (2013.01)

(58) Field of Classification Search
USPC .............. 606/62–68, 246–279, 300–321; 623/13.11–13.2
See application file for complete search history.

(56) References Cited

U.S. PATENT DOCUMENTS

| | | | |
|---|---|---|---|
| 5,704,938 A * | 1/1998 | Staehlin | A61B 17/7216 606/105 |
| 6,375,682 B1 | 4/2002 | Fleischmann et al. | |
| 6,416,516 B1 | 7/2002 | Stauch et al. | |
| 6,706,042 B2 | 3/2004 | Taylor | |
| 7,063,706 B2 * | 6/2006 | Wittenstein | A61B 17/7216 606/90 |
| 7,357,635 B2 | 4/2008 | Belfor et al. | |
| 7,458,981 B2 | 12/2008 | Fielding et al. | |
| 7,531,002 B2 | 5/2009 | Sutton et al. | |
| 7,601,156 B2 | 10/2009 | Robinson | |
| 7,611,526 B2 | 11/2009 | Carl et al. | |
| 7,666,184 B2 | 2/2010 | Stauch | |
| 7,776,091 B2 | 8/2010 | Mastrorio et al. | |
| 7,794,476 B2 | 9/2010 | Wisnewski | |
| 7,811,328 B2 | 10/2010 | Molz, IV et al. | |
| 7,887,566 B2 | 2/2011 | Hynes | |
| 8,043,299 B2 | 10/2011 | Conway | |
| 8,105,363 B2 | 1/2012 | Fielding et al. | |
| 8,147,517 B2 | 4/2012 | Trieu et al. | |
| 8,147,549 B2 | 4/2012 | Metcalf, Jr. et al. | |
| 8,177,789 B2 | 5/2012 | Magill et al. | |
| 8,211,179 B2 | 7/2012 | Molz, IV et al. | |
| 8,216,275 B2 | 7/2012 | Fielding et al. | |
| 8,221,420 B2 | 7/2012 | Keller | |
| 8,241,331 B2 | 8/2012 | Arnin | |
| 8,252,063 B2 | 8/2012 | Stauch | |
| 8,282,671 B2 | 10/2012 | Connor | |
| 8,298,240 B2 | 10/2012 | Giger et al. | |
| 8,419,801 B2 | 4/2013 | DiSilvestro et al. | |
| 8,439,915 B2 | 5/2013 | Harrison et al. | |
| 8,469,908 B2 | 6/2013 | Asfora | |
| 8,486,110 B2 | 7/2013 | Fielding et al. | |
| 8,529,606 B2 | 9/2013 | Alamin et al. | |
| 8,562,653 B2 | 10/2013 | Alamin et al. | |
| 8,568,457 B2 | 10/2013 | Hunziker | |
| 8,632,544 B2 | 1/2014 | Haaja et al. | |
| 8,641,723 B2 | 2/2014 | Connor | |
| 8,663,285 B2 | 3/2014 | Dall et al. | |
| 8,777,947 B2 | 7/2014 | Zahrly et al. | |
| 8,790,409 B2 | 7/2014 | Van den Heuvel et al. | |
| 8,870,959 B2 | 10/2014 | Arnin | |
| 8,894,663 B2 | 11/2014 | Giger et al. | |
| 8,961,567 B2 | 2/2015 | Hunziker | |
| 8,968,406 B2 | 3/2015 | Arnin | |
| 8,992,527 B2 | 3/2015 | Guichet | |
| 9,022,917 B2 | 5/2015 | Kasic et al. | |
| 2004/0023623 A1 | 2/2004 | Stauch et al. | |
| 2004/0181234 A1 * | 9/2004 | McDevitt | A61B 17/0401 606/104 |
| 2005/0090823 A1 | 4/2005 | Bartimus | |
| 2005/0159754 A1 | 7/2005 | Odrich | |
| 2005/0267485 A1 | 12/2005 | Cordes et al. | |
| 2006/0036246 A1 | 2/2006 | Carl et al. | |
| 2006/0047282 A1 * | 3/2006 | Gordon | A61B 17/7022 606/86 A |
| 2006/0058792 A1 | 3/2006 | Hynes | |
| 2006/0235424 A1 | 10/2006 | Vitale et al. | |
| 2006/0293683 A1 | 12/2006 | Stauch | |
| 2007/0010814 A1 | 1/2007 | Stauch | |
| 2007/0264605 A1 | 11/2007 | Belfor et al. | |
| 2008/0033436 A1 | 2/2008 | Song et al. | |
| 2008/0097487 A1 | 2/2008 | Schwab | |
| 2008/0161933 A1 | 7/2008 | Grotz et al. | |
| 2008/0167685 A1 | 7/2008 | Allard et al. | |
| 2008/0228186 A1 | 9/2008 | Gall et al. | |
| 2008/0255615 A1 | 10/2008 | Vittur et al. | |
| 2009/0012565 A1 | 1/2009 | Sachs et al. | |
| 2009/0076597 A1 | 3/2009 | Dahlgren et al. | |
| 2009/0093890 A1 * | 4/2009 | Gelbart | A61B 17/7062 623/24 |
| 2009/0112207 A1 | 4/2009 | Walker et al. | |
| 2009/0171356 A1 | 7/2009 | Klett | |
| 2009/0192514 A1 | 7/2009 | Feinberg et al. | |
| 2009/0245088 A1 * | 10/2009 | Takeuchi | H04L 5/0087 370/210 |
| 2010/0063542 A1 * | 3/2010 | van der Burg | A61B 17/0401 606/232 |
| 2010/0094302 A1 | 4/2010 | Pool et al. | |
| 2010/0100185 A1 | 4/2010 | Trieu et al. | |
| 2010/0121323 A1 | 5/2010 | Pool et al. | |
| 2010/0191248 A1 | 7/2010 | Mehta et al. | |
| 2010/0249847 A1 | 9/2010 | Jung et al. | |
| 2010/0256684 A1 | 10/2010 | Seme et al. | |
| 2010/0280551 A1 | 11/2010 | Pool et al. | |
| 2010/0318129 A1 | 12/2010 | Seme et al. | |
| 2010/0324600 A1 | 12/2010 | Biyani | |
| 2011/0054536 A1 | 3/2011 | Elsebaie et al. | |
| 2011/0060336 A1 * | 3/2011 | Pool | A61B 17/7216 606/57 |
| 2011/0066188 A1 | 3/2011 | Seme et al. | |
| 2011/0106165 A1 | 5/2011 | Schwab et al. | |
| 2011/0230883 A1 * | 9/2011 | Zahrly | A61B 17/7216 606/63 |
| 2011/0238126 A1 | 9/2011 | Soubeiran | |
| 2011/0257655 A1 | 10/2011 | Copf, Jr. | |
| 2012/0053633 A1 | 3/2012 | Stauch | |
| 2012/0088953 A1 | 4/2012 | King | |
| 2012/0109207 A1 | 5/2012 | Trieu | |
| 2012/0203282 A1 | 8/2012 | Sachs et al. | |
| 2012/0283781 A1 | 11/2012 | Arnin | |
| 2013/0096677 A1 | 4/2013 | Myers et al. | |
| 2013/0172940 A1 | 7/2013 | Skaggs | |
| 2013/0253344 A1 | 9/2013 | Griswold et al. | |
| 2013/0296940 A1 | 11/2013 | Northcutt et al. | |
| 2014/0005788 A1 | 1/2014 | Haaja et al. | |
| 2014/0025172 A1 | 1/2014 | Lucas et al. | |
| 2014/0114311 A1 | 4/2014 | Pool et al. | |
| 2014/0128868 A1 * | 5/2014 | Harrison | A61B 17/66 606/60 |
| 2014/0128920 A1 | 5/2014 | Kantelhardt | |
| 2014/0142631 A1 | 5/2014 | Hunziker | |
| 2014/0214034 A1 | 7/2014 | Rayes | |
| 2014/0236234 A1 * | 8/2014 | Kroll | A61B 17/7014 606/264 |
| 2014/0296918 A1 | 10/2014 | Fening et al. | |
| 2014/0303538 A1 | 10/2014 | Baym et al. | |
| 2014/0303539 A1 | 10/2014 | Baym et al. | |
| 2014/0324047 A1 | 10/2014 | Zahrly et al. | |
| 2014/0358150 A1 | 12/2014 | Kaufman et al. | |
| 2015/0105824 A1 | 4/2015 | Moskowitz et al. | |
| 2015/0313745 A1 * | 11/2015 | Cheng | A61B 17/72 602/19 |

OTHER PUBLICATIONS

Bodo, A., Hangody, L., Borsitzky, B., Beres, G., Arato G., Nagy, P., Rathonyi, G. "Development of a tension-adjustable implant for anterior cruciate ligament reconstruction", Eklem Hastaliklari ve Cerrahisi—Joint Diseases and Related Surgery, 2008, vol. 19, No. 1, pp. 27-32, Turkish Joint Diseases Foundation, Ankara, Turkey.

* cited by examiner

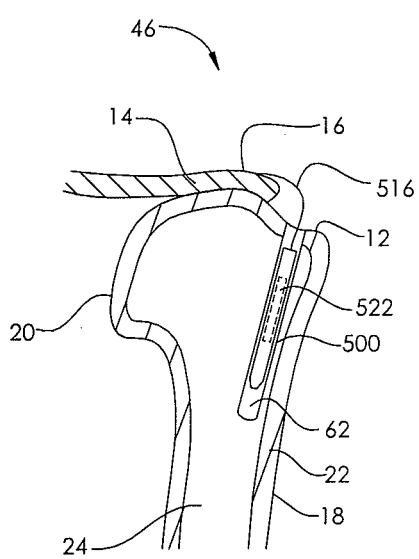 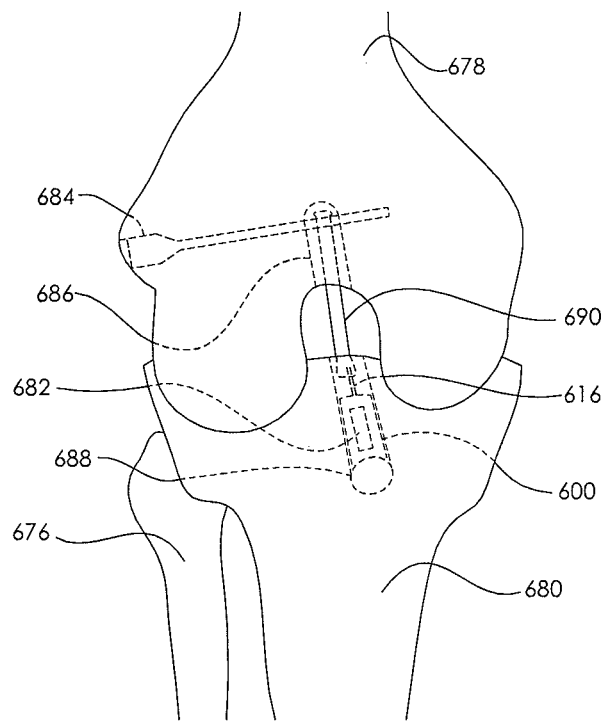
FIG. 11
FIG. 12

NONINVASIVELY ADJUSTABLE SUTURE ANCHORS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

The field of the invention generally relates to medical devices for attaching soft tissue to bone.

Description of the Related Art

In many common surgical techniques, soft tissue (muscle, tendon, ligament) is secured to the bone using a variety of types of tissue anchors. In most of these surgeries, it is important that that the connection between the soft tissue and the bone remain consistent, without significant degradation after surgery and recovery, both short term and long term. One common method of securing soft tissue to bone is with a suture anchor, which is sutured or otherwise attached to the particular portion of soft tissue and then anchored to the bone. The anchoring to the bone may be achieved by a threaded screw, or several other types of securement.

One of the common complications of many of these surgical techniques is for the connection between the soft tissue and the bone to degrade. For example, the healing of the tissue may cause the tensile force at which the soft tissue is secured to the bone to increase or decrease. Also, the length of the connection may increase or decrease, creating such effects as too much joint motion, too little joint motion, hyperextension, and of course fatigue and pain. Laxity of a suture is a common occurrence, and can increase the variance in the final tension in the connection of the soft tissue to the bone.

Rotator cuff injury is one of the most common ailments of the shoulder. The rotator cuff is a group of muscles and tendons that stabilize the shoulder joint. Many of the injuries to the rotator cuff are able to be treated without surgery, for example, certain cases of tendonitis and other traumatic injuries. Often, the injury to the rotator cuff involves the tearing of the tendons that attach one or more of the rotator cuff muscles to the humerus (upper arm) bone. Active patients who have substantial or complete tears of one of more portions of the rotator cuff are often treated by rotator cuff surgery. Rotator cuff tears are sometimes classified as small (<1 cm), medium (1 cm to 3 cm), large (3 cm to 5 cm), and massive (>5 cm). They are also characterized by shape, such as transverse, L-shaped, linear, crescent, and triangular. Rotator cuff surgery may be performed as an open surgery, a mini-open surgery (wherein the deltoid muscle need not be detached during surgery), or an arthroscopic surgery. Many different suture techniques are used, each attempting to improve upon strength, stability, safety and procedural speed and invasiveness. In certain groups of patients, postoperative stiffness develops. This may happen in more than 8% of patient under the age of 50, and in more than 15% of patients who also have either calcific tendonitis or adhesive capsulitis. Many patients with postoperative stiffness choose to undergo subsequent arthrosopic procedures to remove or remodel scar tissue. Re-tears are also somewhat common after the recovery following the initial rotator cuff surgery, with reported rates between 4% to 26%.

Anterior cruciate ligament (ACL) injury is common in athletes in a variety of sports, especially in contact sports, with the ACL. ACL reconstruction surgery is often performed after tear or rupture of the ACL, and usually includes the removal of the damaged ligament and replacement with a graft. The graft may be an autograft (a portion of the patient's own patellar tendon or hamstring) or an allograft (cadaveric patellar tendon, anterior tibialis tendon, or Achilles tendon). This surgery is commonly performed arthroscopically, with the graft inserted into tunnels created in the tibia and femur, and then secured to these bones with tissue anchors. Post-recovery, some ACL reconstruction patients have persistent loss in range of motion, in either flexion or extension, which may be due to imprecise placement of the graft during the initial surgery or the healing process itself. A classification system has been proposed that includes four different grades: Type 1: less than a 10° loss of extension with normal flexion, Type 2: more than a 10° loss of extension with normal flexion, Type 3: more than a 10° loss of extension with a flexion deficit of greater than 25°, and Type 4: more than a 20° loss of extension with a flexion deficit greater than 30°. Some of these patients are able to improve through rehabilitation, but others require an additional surgical procedure.

Despite the wide variety of available devices for anchoring soft tissue (e.g. tendon) to bone, there remains a need for an implant which can be adjusted post-operatively to increase or decrease tension without the need for additional surgical intervention.

SUMMARY OF THE INVENTION

In a first embodiment of the invention, an adjustable implant system includes a bone anchor having a first end and a second end, and including a bone engagement surface adjacent the first end, the bone anchor further comprising a housing extending between the first end and the second end. The adjustable implant system further includes a driving element carried within the housing and configured for non-invasive actuation, wherein the driving element is coupled to an adjustment component, the adjustment component configured for coupling to a flexible elongate tension member capable of engaging soft tissue of a patient, wherein non-invasive actuation of the driving element causes the adjustment component to change the amount of tension on the flexible elongate tension member. The adjustable implant system further includes an external adjustment device comprising at least one energy transferring component and configured to be placed on or adjacent the skin of the patient, and wherein the at least one energy transferring component of the external adjustment device is configured to energize the driving element inside the housing of the adjustable implant.

In another embodiment of the invention, a method of treating a patient includes the steps of providing a tensioning device having a connector for connection to soft tissue, and a drive for drawing the connector in the direction of the tensioning device, inserting the tensioning device into a bone, and connecting the connector to soft tissue, wherein the tensioning device is configured to draw the connector in the direction of the tensioning device in response to a wireless signal.

BRIEF DESCRIPTION OF THE DRAWINGS

FIG. 11 illustrates a humerus with a hole drilled for placement of an adjustable suture anchor in a rotator cuff patient.

FIG. 12 illustrates a tibia with a hole drilled for placement of an adjustable suture anchor in an anterior cruciate ligament patient.

DETAILED DESCRIPTION OF THE ILLUSTRATED EMBODIMENTS

Figure 1:
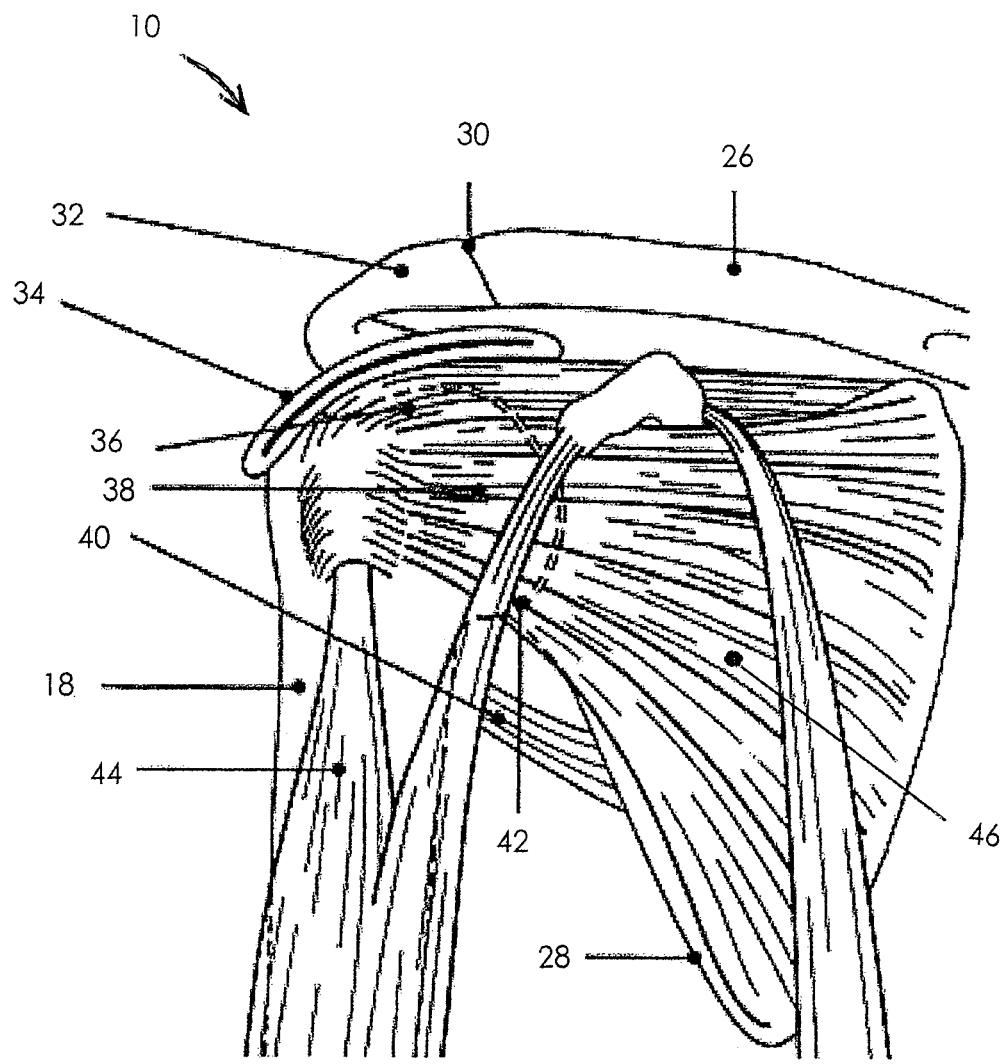
FIG. 1 illustrates the human shoulder.
Figure 2:
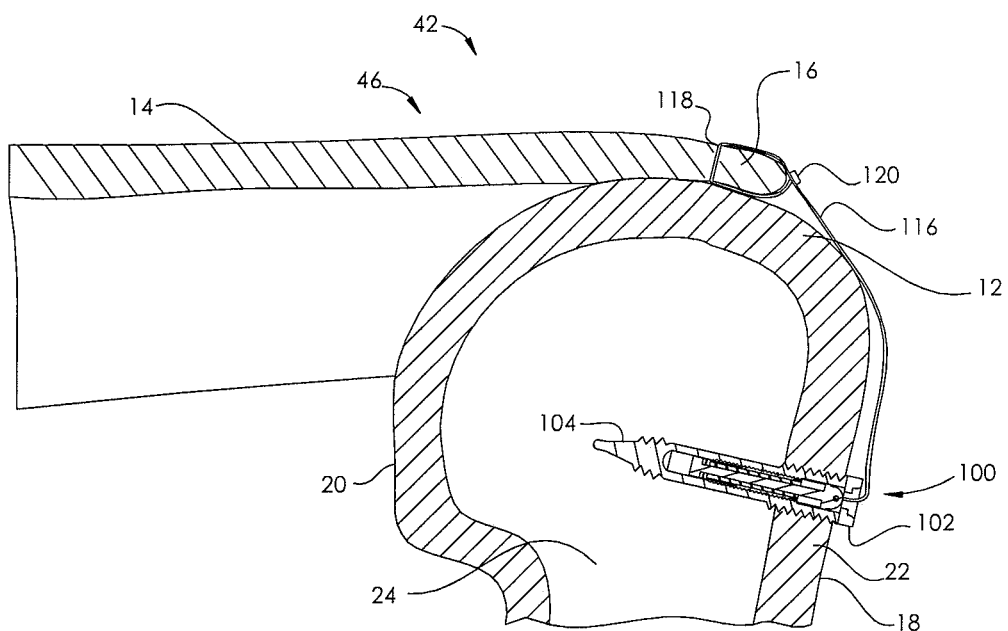
FIG. 2 illustrates a cross-section of an embodiment of an adjustable suture anchor secured in the humerus of a rotator cuff surgery patient.

FIG. 1 illustrates an anatomical view of a human shoulder 10, which includes the following bones: scapula 28, clavicle 26 and humerus 18 The glenohumeral joint 42 (or shoulder joint) is an articulation between the scapula 28 and the head 20 of the humerus 18, the head 20 visible in a cross-sectional view in FIG. 2. The acromion 32 is a bony process on the scapula 28 which articulates with the clavicle 26 at the acromioclavicular joint 30. There is very little interface between the humerus 18 and the scapula 28 in the glenohumeral joint 42 making it the most mobile joint in the human body. The rotator cuff 46 is a group of muscles and their respective tendons which serve to stabilize the shoulder 10, including the supraspinatus 36, infraspinatus (not visible in FIG. 1), subscapularis 38, and teres minor 40. All four of these muscles arise from different portions of the scapula 28 and attach via their respective tendons to either the greater tubercle 12 of the humerus 18, which is lateral to the humeral head 20 or the lesser tubercle (not shown). Also shown in FIG. 1 is the bursa 34, a fluid-filled sac which cushions the bones, muscles and tendons of the glenohumeral joint 42. Additionally, the biceps muscle 44 is show for perspective purposes.

Figures 3, 4:
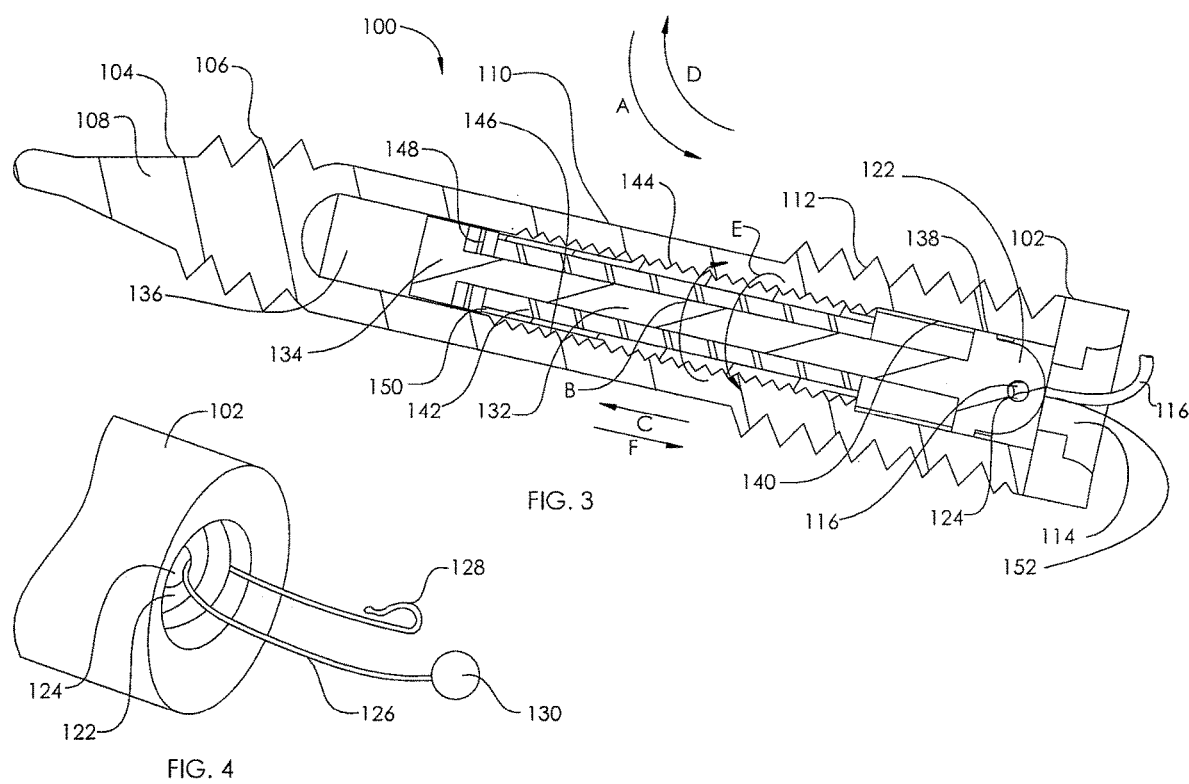
FIG. 3 illustrates a detailed cross-sectional view of the adjustable suture anchor of FIG. 2.
FIG. 4 illustrates a first end of the adjustable suture anchor supplied with a threading tool.

A simplified cross-sectional view of the shoulder 10 is shown in FIG. 2, with an embodiment of an adjustable suture anchor 100 implanted within the shoulder 10. The adjustable suture anchor 100 has a first end 102 and a second end 104, the second end 104 configured for insertion through cancellous bone 24 and the first end 102 configured for securing in the cortical bone 22 of the humerus 18. In FIG. 3 detail of the second end 104 shows a tapered thread 106 and a tapered tip 108, which can aid in driving the adjustable suture anchor 100 through the humerus 18. Alternatively, an initial hole may be reamed in the cortical bone 22 and cancellous bone 24 to aid in the insertion of the adjustable suture anchor 100. A housing 110 extends between the first end 102 and second end 104 of the adjustable suture anchor 100. At the first end 102, a threaded portion 112 is provided which allows a secure interface with the cortical bone 22. The threaded portion 112 may be of a single major diameter (for example with a minor diameter that increases towards the first end), or the major diameter may vary from smaller to larger as it approaches the first end 102. The threaded portion 112 may be provided with cutting threads, in order to better create the interface with the cortical bone 22. A keyed cavity 114 is provided in the first end 102 for interfacing with a driving tool. The shapes of both the driving tool and the keyed cavity 114 may be hexagonal, cross-shaped, star-shaped or a number of other keyed shapes that allow a maximal torque in securing the adjustable suture anchor 100 into the humerus 18.

A simplified rotator cuff 46 is represented in FIG. 2 by a muscle 14 and its tendon 16, in cross-section. In this embodiment of the adjustable suture anchor 100, a suture 116 is secured to the tendon 16 through at least one puncture 118. The suture 116 is held in place with one or more knots 120, which may comprise a number of different knot types. Any of the possible suturing techniques are envisioned, including: single-row technique, double-row techniques, diamond, mattress double anchor, or modified mattress double anchor.

The adjustable suture anchor 100 contains within its housing 110 an adjustable component 122 having an eyelet 124. The eyelet 124 is configured for securing an end of the suture 116. As shown in FIG. 4, the adjustable suture anchor 100 is supplied with a threading tool 126, which can be used to aid the placement of the suture 116 through the eyelet 124 of the adjustable component 122. The suture 116 is looped through or tied to a hook 128 in the threading tool 126, and then the threading tool 126 is pulled from gripping structure 130 at the opposite end of the threading tool 126 from the hook 128. The suture 116 is pulled through the eyelet 124 of the adjustable component 122 and tied or otherwise secured in place. The suture 116 is tied with the desired amount of tension.

The adjustable component 122 of the adjustable suture anchor 100 further includes a shaft 132 and a base 134 at the opposite end of the shaft 132 from the eyelet 124. The adjustable component 122 is configured to be axially movable within a longitudinal cavity 136 of the housing 110. Fins 138 are slidable within longitudinal grooves 140 in the longitudinal cavity 136 of the housing 110, thus inhibiting the rotation of the adjustable component 122 in relation to the housing 110. The hollow magnet 142 is radially poled, and is bonded within a threaded magnet housing 144. The threaded magnet housing 144 threadingly engages an internal thread 146 of the housing 110. A thrust bearing 148 is disposed between the base 134 of the adjustable component 122 and a first end 150 of the threaded magnet housing 144. If it is desired during or particularly after surgery to tighten the tension on the suture 116, a moving magnetic field is applied externally to the patient in a first rotational direction A, causing the hollow magnet 142 and threaded magnet housing 144 to spin in a second rotational direction B. Because it is secured to the hollow magnet 142, the threaded magnet housing 144 therefore turns within the internal thread 146 of the housing 110, actuating it in a first axial direction C. As the first end 150 of the threaded magnet housing 144 pushes against the thrust bearing 148 and the base 134 of the adjustable component 122, the adjustable component 122 is moved in the first axial direction C. This shortens the effective length of the suture 116, and thus increases its tensile force, which is the force it applies to the tendon 16. This ability to adjust the tension on the suture 16 non-invasively on an awake, mobile patient, make it possible to assure the ideal state of the shoulder 10 during the healing process. To isolate the longitudinal cavity 136 of the housing (and its contents) from body fluids, a seal 152 is carried near the first end 102 of the adjustable suture anchor 100. The suture 116 is able to move within this seal 152 (o-ring or slit diaphragm) without causing any significant material to enter the longitudinal cavity 136. If the tension on the suture 116 is higher than desired, a moving magnetic field is applied externally to the patient in a rotational direction D (opposite A), causing the hollow magnet 142 and threaded magnet housing 144 to spin in a rotational direction E (opposite B). This moves the adjustable component in an axial direction F (opposite C). The tension on the suture 116 is thus lowered.

Figure 5:
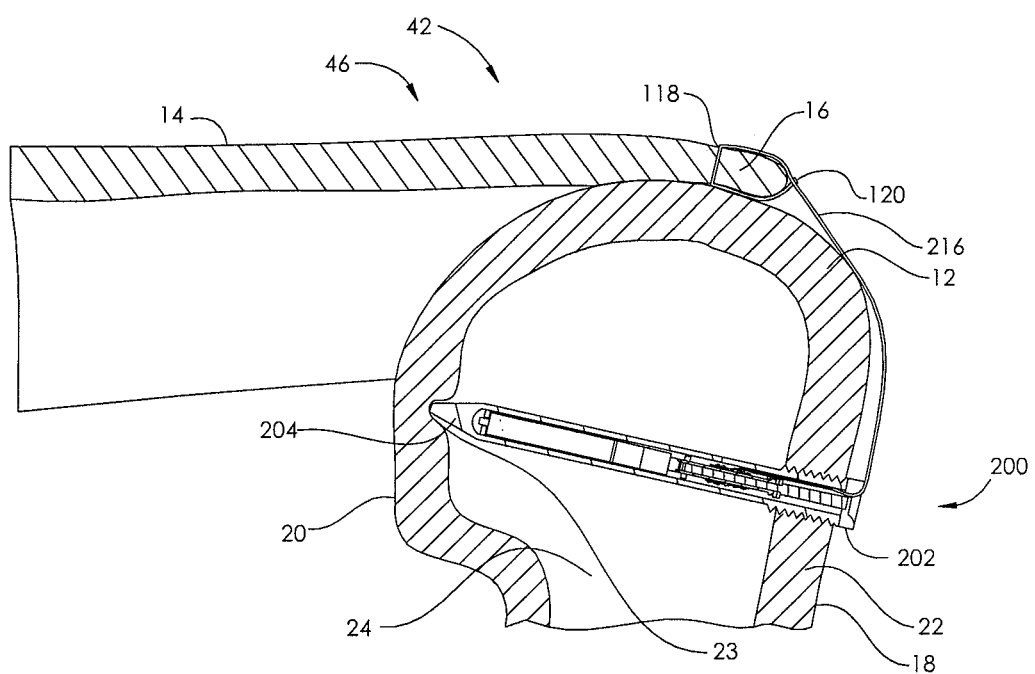
FIG. 5 illustrates a cross-section of an embodiment of an adjustable suture anchor secured in the humerus of a rotator cuff surgery patient.
Figure 6:
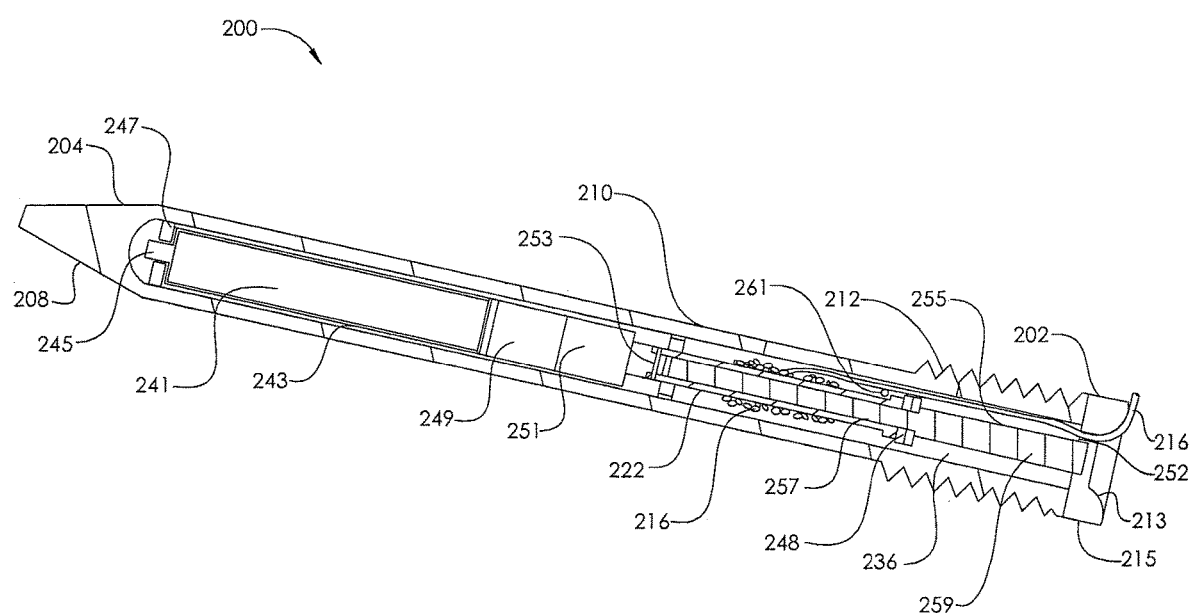
FIG. 6 illustrates a detailed cross-section view of the adjustable suture anchor of FIG. 5.

Turning now to FIG. 5, a different embodiment of an adjustable suture anchor 200 is depicted in its implanted configuration within the humerus 18. The adjustable suture anchor 200 has a first end 202 and a second end 204. As seen in more detail in FIG. 6, the second end 204 includes a tapered tip 208, to aid in insertion through the cancellous bone 24. A pilot hole may be drilled through the cortical bone 24 and the cancellous bone 24, and an additional pocket 23 may be drilled, into which the tapered tip 208 may reside, for increased stability. A threaded portion 212 is provided adjacent the first end 202 of the adjustable suture anchor 200 for engaging with the cortical bone 24. A keyed outer surface 215, having for example a hexagonal shape, is provided for tightening the adjustable suture anchor into humerus 18. In this embodiment, suture 216 extends from a longitudinal cavity 236 within a housing 210 of the adjustable suture anchor. The suture 216 is partially wound on a spool 222, which is rotatable within the longitudinal cavity 236. The suture 216 can slide through a seal 252, which protects the longitudinal cavity 236 from body fluids. The first end 202 of the adjustable suture anchor 200 includes a radiused surface 213, which allows the suture 216 to be slid over it without fraying. A rotatable cylindrical radially-poled magnet 241 bonded within a magnet housing 243 having a pin 245. The magnet housing 243 is constrained axially within the longitudinal cavity 236. The pin 245 turns within a radial bearing 247. The magnet housing 243 connects to a first planetary gear stage 249, which connects to a second planetary gear stage 251. The second planetary gear stage 251 is coupled to the spool 222 by a pin 253. After implanting the adjustable suture anchor 200 into the humerus 18, the suture 216 is pulled partially out of the longitudinal cavity 236 and secured to a tendon 16 via a puncture 118. The suture is tied in a knot 120 so that it is at the desired amount of tension.

If at a later time, for example after surgery, the tension on the suture 216 is higher than desired, a moving magnetic field is applied externally to the patient in a first rotational direction, causing the magnet 241 to be turned, and thus the first and second planetary gear stages 249, 251 and spool 222. Because of the gear reduction from the first and second planetary gear stages 249, 251, the spool 222 is turned at a slower rotational speed than the magnet 241, allowing precision adjustment of the tension in the suture 216. The gearing also allows the desired tension to be achievable without an undesirably large applied moving magnetic field, for example a field that is above International Commission on Non-Ionizing Radiation Protection (ICNIRP) guidelines for current density in body tissues and fluids, for example 0.04 Amperes/m$^2$ or less. As the spool 222 is turned the suture 216 is pulled into the longitudinal cavity 236 through the seal 252, tightening the tension in the suture 216, and thus on the tendon 16. A stepped post 255 is secured to the first end 202 of the adjustable suture anchor 200. A thrust bearing 248 and the spool 222 are both carried on a small diameter portion 257 of the stepped post 255. When the suture 216 is in tension, the spool 222 is forced against the thrust bearing 248, which in turn is forced against the edge of a large diameter portion 259 of the stepped post 255, thus minimizing the rotational resistance of the spool 222. The suture 216 passes through a guide loop 261 to aid its takeup onto the spool 222. In both the adjustable suture anchor 100 and adjustable suture anchor 200, a pulley may be carried by the first end 102, 202 to serve the function of the radiused surface 213, both in keeping the suture 116, 216 from fraying, and in changing the direction of the of the suture 116, 216 which is in tension.

Figure 7:
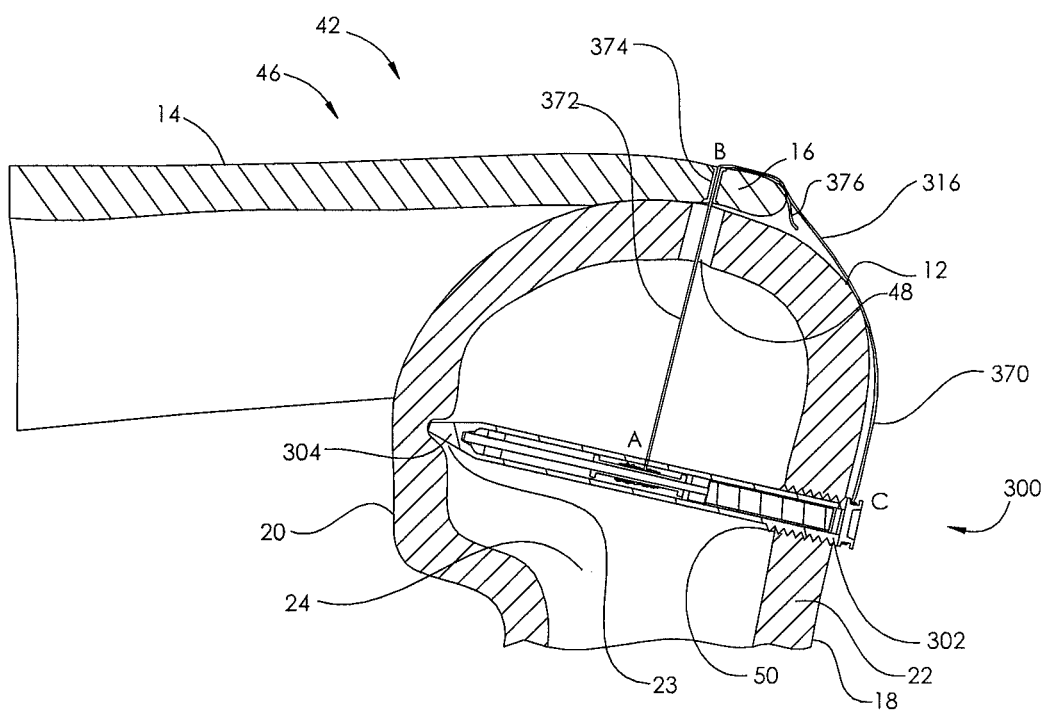
FIG. 7 illustrates a cross-section of an embodiment of an adjustable anchor secured in the humerus of a rotator cuff surgery patient.
Figure 8:
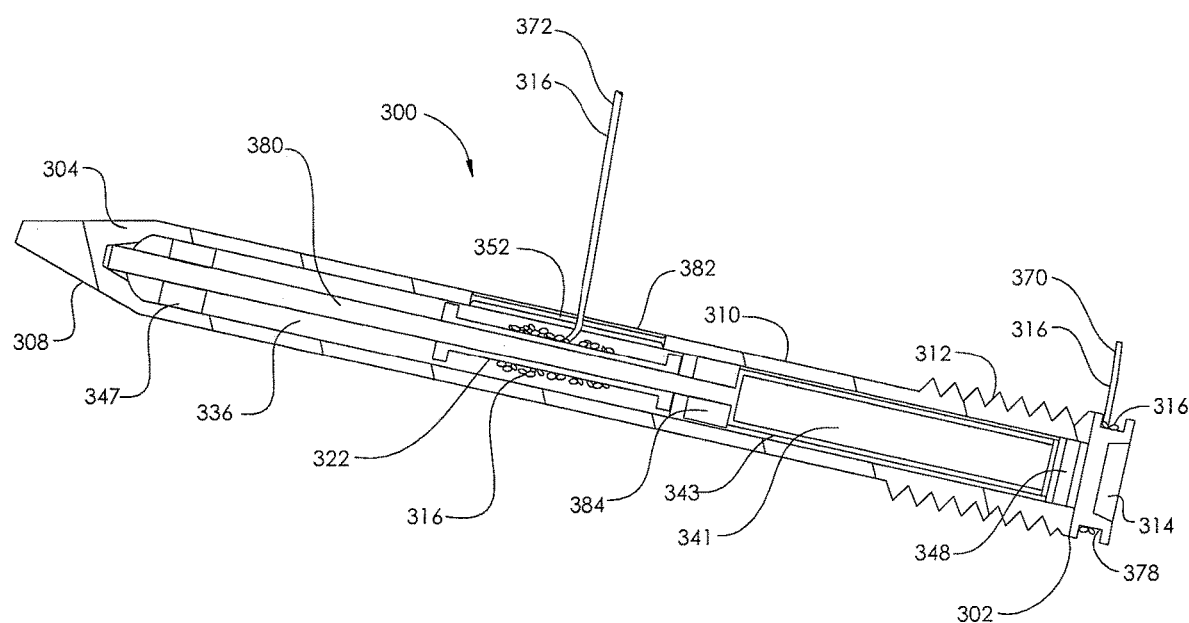
FIG. 8 illustrates a detailed cross-section view of the adjustable suture anchor of FIG. 7.

A different embodiment of an adjustable suture anchor 300 is depicted in FIGS. 7 and 8. In this embodiment, a loop of suture 316 extends from the tendon 16 in an external portion 370 and an internal portion 372. A tunnel 374 through which the suture 316 can slide is made in the tendon 16, so that the length of the loop of suture 316 which extends from point A to point B to point C, can be adjusted, thus adjusting the tension with which the suture 316 holds the tendon 16. A pad 376 of biocompatible material is placed underneath the suture 316 to minimize damage to the tendon as the suture 316 slides over it. A first end 302 of the adjustable suture anchor 300 includes a threaded portion 312 and an external circumferential groove 378, around which external portion 370 of suture 316 can be wrapped and/or tied. A second end 304 of the adjustable suture anchor 300 has a tapered tip 308, which may be used as described in the prior embodiments. Within the longitudinal cavity 336 of the housing 310 of the adjustable suture anchor 300, a cylindrical, radially poled magnet 341 is bonded within a magnet housing 343, which is secured to a rotating shaft 380. The magnet housing 343 and shaft 380 are rotatably held between a radial bearing 347 and a thrust bearing 348. A spool 322 is secured to the shaft 380 so that rotation of magnet 341 causes rotation of the shaft. A spacer 384 is disposed between the spool 322 and the magnet 341 and secured to the housing 310. A seal or diaphragm 352 is carried within an aperture 382 in the lateral wall of the housing 310, allowing the internal portion 372 of the loop of suture 316 to move in and out of the housing 310 of the adjustable suture anchor 300, with the contents of the longitudinal cavity 336 remaining protected from body fluids.

During implantation, two pilot holes are drilled through which through the cortical bone 22 and cancellous bone 24, a first hole 50 extending from point C towards point A. The first hole may even be extended to create an additional pocket 23. A second hole 48 extends from point B towards (and just past) point A. A grasper tool is placed through hole 48, and a suture insertion tool inserts the end of the external portion 370 of the suture 316 through hole 50. The grasper tool grasps the suture 316 and pulls it out through hole 48. The adjustable suture anchor is then inserted and secured inside hole 50, tightening it with a driving tool inserted into a keyed cavity 314. The housing may be oriented so that the aperture 382 extends in a direction towards hole 48. The external portion 370 of the suture 316 is now placed through the tunnel 374 in the tendon 16, and then wrapped and/or tied around the external circumferential groove 378, thus closing the loop in the suture 316. To adjust the tension of the suture 316, a moving magnetic field is applied externally to the patient in a first rotational direction, causing the magnet 341 to turn and the spool 322 to tighten the tension in the suture 316. The moving magnetic field may be applied in an opposite rotational direction in order to loosen the tension in the suture 316.

Figure 9:
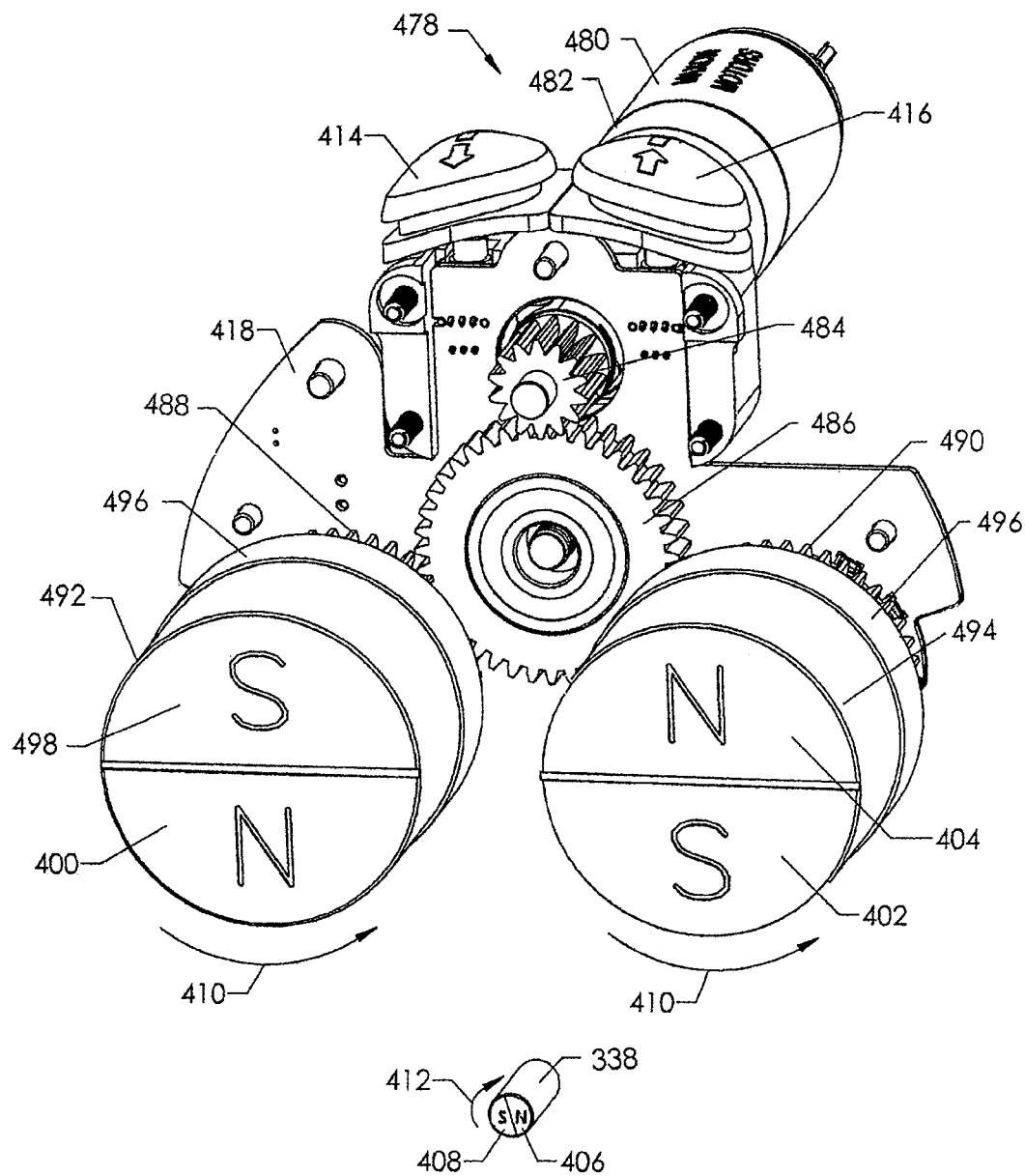
FIG. 9 illustrates internal components of an external adjustment device for non-invasively adjusting an adjustable suture anchor according to one embodiment.
Figure 10:
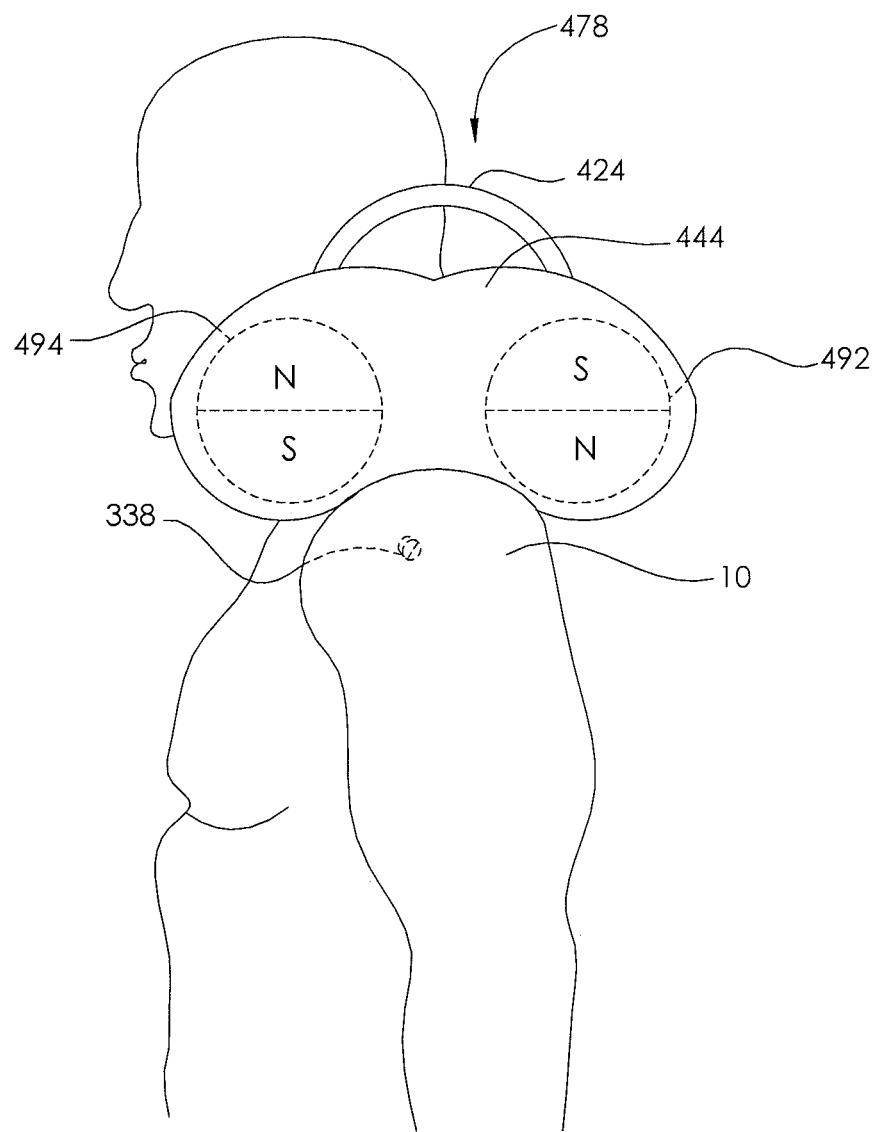
FIG. 10 illustrates an external adjustment device in a configuration for adjusting an adjustable suture anchor implanted within the humerus.

FIGS. 9 and 10 illustrate an external adjustment device 478 configured for applying a moving magnetic field to allow for non-invasive adjustment of the adjustable suture anchor 100, 200, 300 by turning the magnet 142, 241, 341 within the adjustable suture anchor 100, 200, 300. FIG. 9 illustrates the internal components of the external adjustment device 478, and for clear reference, shows a simplified version 338 of the magnet 142, 241, 341 of the adjustable suture anchor 100, 200, 300, without the rest of the assembly. The internal working components of the external adjustment device 478 may, in certain embodiments, be similar to that described in U.S. Patent Application Publication No. 2012/0004494. A motor 480 with a gear box 482 outputs to a motor gear 484. The motor gear 484 engages and turns a central (idler) gear 486, which has the appropriate number of teeth to turn first and second magnet gears 488, 490 at identical rotational speeds. First and second magnets 492, 494 turn in unison with the first and second magnet gears 488, 490, respectively. Each magnet 492, 494 is held within a respective magnet cup 496 (shown partially). An exemplary rotational speed is 60 RPM or less. This speed range may be desired in order to limit the amount of current density induced in the body tissue and fluids, to meet international guidelines or standards. As seen in FIG. 9, the south pole 498 of the first magnet 492 is oriented the same as the north pole 404 of the second magnet 494, and likewise, the first magnet 492 has its north pole 400 oriented the same as the south pole 402 of the second magnet 494. As these two magnets 492, 494 turn synchronously together, they apply a complementary and additive moving magnetic field to the radially-poled, magnet 338, having a north pole 406 and a south pole 408. Magnets having multiple north poles (for example, two) and multiple south poles (for example, two) are also contemplated in each of the devices. As the two magnets 492, 494 turn in a first rotational direction 410 (e.g., counter-clockwise), the magnetic coupling causes the magnet 338 to turn in a second, opposite rotational direction 412 (e.g., clockwise). The rotational direction of the motor 480 is controlled by buttons 414, 416. One or more circuit boards 418 contain control circuitry for both sensing rotation of the magnets 492, 494 and controlling the rotation of the magnets 492, 494.

FIG. 10 shows the external adjustment device 478 for use with an adjustable suture anchor 100, 200, 300 placed in the humerus. The external adjustment device 478 has a first handle 424 attached to a housing 444 for carrying or for steadying the external adjustment device 478, for example, steadying it against a shoulder 10, as in FIG. 10, or against a knee, in the case of an adjustable anchor for anterior cruciate ligament attachment. The external adjustment device 478 includes a control panel including a display (not shown). Control circuitry contained on circuit boards 418 may be used by the surgeon to store important information related to the specific aspects of each particular patient. The external adjustment device 478 may be able to receive and transfer information via an SD card or USB device, or by wireless input. An additional feature is a camera at the portion of the external adjustment device 478 that is placed over the skin. For example, the camera may be located between the first magnet 492 and the second magnet 494. The skin directly over the implanted magnet 338 may be marked with indelible ink. A live image from the camera is then displayed on the display 448 of the control panel 446, allowing the user to place the first and second magnets 492, 494 directly over the area marked on the skin. Crosshairs can be overlayed on the display over the live image, allowing the user to align the mark on the skin between the crosshairs, and thus optimally place the external adjustment device 478.

FIG. 11 illustrates an alternative geometry for creating a hole 62 at the greater tubercule 12 of the humerus 18. An adjustable suture anchor 500 having an adjustable component 522 is implanted in the hole 62 and is capable of adjusting the tension in a suture 516, which is attached to a tendon 16 of a rotator cuff 46. The hole 62 is parallel the axis of the humerus 18, and thus allows for a longer length adjustable suture anchor 500. This makes possible an adjustable suture anchor 500 with more planetary gear sets and allow allows for a greater range of adjustability (length, tension).

Though the adjustable suture anchors 100, 200, 300, 500 as described are adapted for attaching the tendon of the rotator cuff to the humerus, it is conceived that similar suture anchors would be useful for adjusting other soft tissue attachments to bone. Some examples include the anterior cruciate ligament (ACL) in one or both of its attachment point to the bone (femur and/or tibia). FIG. 12 shows a configuration for an adjustable suture anchor 600 for adjusting the tension in a graft 690 for replacing the ACL (for example a portion of the patellar tendon). The graft 690 is secured in a femoral tunnel 686 in a femur 678 with a traditional tissue anchor 684. The tissue anchor 684 may be metallic, or may be of a resorbable material. The adjustable suture anchor 600 is anchored to bone inside a tibial tunnel 688 created in a tibia 680. An adjustable component 682 within the adjustable suture anchor 600 adjusts the tension in a suture 616 which is attached to the graft 690. The diameter of the tissue anchor 684 may be less than about 14 mm, or preferably less than about 12 mm. The length of the femoral tunnel 686 may be on the order of about 25 mm to about 35 mm.

An alternative ligament for which the adjustable suture anchors 100, 200, 300, 500, 600 may be used is the medial collateral ligament (MCL) whose attachment points are the femur 678 and tibia 680. The lateral collateral ligament (LCL), whose attachment points are the femur 678 and fibula 676, may also be adjustably attached by a modified embodiment of the adjustable suture anchor 100, 200, 300, 500, 600. Other tendons and ligaments which may benefit from the adjustability of the adjustable suture anchors 100, 200, 300, 500, 600 include the talo-fibular ligament, the tibial tendon, and the Achilles tendon. Typical ranges of the length of adjustment for the tendon and ligament applications discussed may be typically on the order of less than about 2 cm, or in some embodiments less than about 1 cm.

Other indications for an adjustable connection between soft tissue and bone which may benefit from embodiments of the adjustable suture anchors 100, 200, 300, 500, 600 include adjustable slings attached to the pubic bone, for urinary stress incontinence.

Magnet materials may include rare earth magnets, including Neodymium-Iron-Boron. Rigid components of the adjustable suture anchor may be made from titanium, titanium allows, or other biocompatible materials. In some cases, polyether ether ketone (PEEK) may be an appropriate material. In some cases, at least some components may comprise bioabsorbable materials.

On any of the embodiments presented, it is envisioned that a unidirectional version may be constructed. For example, a ratcheting wheel that allows stepped increases in the rotational direction which increases the tension on the suture, but does not allow the opposite rotational direction to occur. In addition, any of the embodiments may or may not use gearing, for example to increase the deliverable for or increase the precision.

In addition to a threaded screw attachment to the bone, the bone anchor may comprise an interference fit, for example a tack, a bone adhesive interface, or a staple. Additionally pronged, flanged, snagging, barbed, spiked, tabbed or curved anchors may be secured to the bone. Often, multiple anchors are attached in the same patient.

Though magnetic actuating adjustable implants are presented, other non-invasive systems are considered to be within the scope of the adjustable suture anchors described. For example, the adjustable component may be driven by any of a variety of alternative drives such as an implanted motor which may be powered via inductive coupling, internal battery, or hard wired connection via leads that extend percutaneously but may be detached from the implant and removed following a post-surgical adjustment. The adjustable component may instead be driven by an ultrasonically actuated motor, such as a piezoelectric motor manufactured by Actuated Medical of Bellefonte, Pa. The adjustable component may also be driven by a subcutaneous hydraulic or pneumatic pump which pressurizes fluid through a valve when pressure is placed on the skin of the patient, over the pump interface. The adjustable component may also be driven by an implantable shape-memory driven actuator.

The adjustable suture anchors 100, 200, 300, 500, 600 may be configured so that the magnets and magnet housings may be removed from the adjustable suture anchor assembly, using a small minimally invasive incision, leaving the remained of the adjustable suture anchor 100, 200, 300, 500, 600 in place. For example, if magnetic resonance imaging is prescribed for the patient, the magnet may be temporarily or permanently removed, to allow imaging of the implant area.

What is claimed is:

1. An adjustable implant system comprising:
    a bone anchor having a first end and a second end, with a housing extending between the first end and the second end, the bone anchor including a bone engagement surface adjacent the first end configured to engage a bone;
    a flexible elongate tension member extending from the first end and configured to engage a soft tissue of a patient; and
    a driving element at least partially disposed within the housing and coupled to an adjustment component that is operatively coupled to the flexible elongate tension member, the driving element configured for non-invasive actuation in one direction to non-invasively cause an increase in an amount of tension on the flexible elongate tension member and in another direction to non-invasively cause a decrease in the amount of tension on the flexible elongate member thereby changing an amount of tension between the bone and the soft tissue.

2. The adjustable implant system of claim 1, wherein the driving element is selected from the group consisting of: a permanent magnet, an inductively coupled motor, an ultrasonically actuated motor, a subcutaneous hydraulic pump, a subcutaneous pneumatic pump, and a shape-memory driven actuator.

3. The adjustable implant system of claim 1, wherein the driving element comprises a permanent magnet.

4. The adjustable implant system of claim 3, wherein the permanent magnet comprises a rare earth magnet.

5. The adjustable implant system of claim 1, wherein the permanent magnet comprises Neodymium-Iron-Boron.

6. The adjustable implant system of claim 1, wherein the bone anchor secures to the bone by a mechanism selected from the group consisting of: a screw, an interference fit, a tack, an adhesive, a staple, a prong, a flange, a snagging member, a barb, a spike, and a tab.

7. The adjustable implant system of claim 1, wherein the bone anchor comprises an externally threaded portion configured for engaging cortical bone.

8. The adjustable implant system of claim 1, further comprising a seal carried by the bone anchor and configured to seal around the exterior of the flexible elongate tension member.

9. The adjustable implant system of claim 1, further comprising a longitudinal cavity extending along a length of the housing, the longitudinal cavity.

10. The adjustable implant system of claim 1, wherein the adjustable component comprises a spool configured for winding and unwinding the flexible elongate tension member.

11. The adjustable implant system of claim 10, wherein the spool is at least partially disposed within the housing.

12. The adjustable implant system of claim 1, further comprising:
    an external adjustment device comprising at least one energy transferring component and configured to be placed on or adjacent the skin of the patient, wherein the at least one energy transferring component is configured to energize the driving element inside the housing of the bone anchor to change the amount of tension on the flexible elongate tension member.

13. The adjustable implant system of claim 12, wherein the external adjustment device comprises a first radially-poled permanent magnet configured for rotation about a first axis and a second radially-poled permanent magnet configured for rotation about a second axis.

14. The adjustable implant system of claim 13, wherein the first axis is different from the second axis.

15. The adjustable implant system of claim 14, wherein the first axis is parallel to the second axis.

16. The adjustable implant system of claim 1, wherein the adjustable component is configured to be axially moveable within the housing upon actuation of the driving element.

17. The adjustable implant system of claim 1, wherein at least a portion of the bone engaging surface includes a threaded surface.

18. The adjustable implant system of claim 1, further comprising:
    an aperture disposed within a lateral wall of the bone anchor between the first end and the second end.

19. The adjustable implant system of claim 18, wherein a portion of the flexible elongate tension member extends from the aperture and is configured to engage the soft tissue.

* * * * *